United States Patent [19]

Kline

[11] Patent Number: 4,609,353
[45] Date of Patent: Sep. 2, 1986

[54] DENTAL APPARATUS FOR REMOVING CROWNS

[76] Inventor: Joseph M. Kline, 3501 N. Valley St., Arlington, Va. 22207

[21] Appl. No.: 739,794

[22] Filed: May 31, 1985

[51] Int. Cl.$^4$ ............................................... A61C 3/16
[52] U.S. Cl. ................................................ 433/159
[58] Field of Search ........................... 433/159, 158, 6

[56] References Cited

U.S. PATENT DOCUMENTS

| | | | |
|---|---|---|---|
| 989,267 | 4/1911 | Kenney | 433/158 |
| 1,019,519 | 3/1912 | Polin | 433/159 |
| 1,786,127 | 12/1930 | Rado | 433/159 |

Primary Examiner—Robert Peshock
Attorney, Agent, or Firm—Dowell & Dowell

[57] ABSTRACT

An apparatus for removing crowns from teeth wherein the apparatus is a plier-like instrument having upper and lower opposing jaw portions with the lower jaw including a tapered and pointed member for engaging the lower margin of a crown and wherein the upper jaw supports an axially offset and rotatable pin member which may be adjustably positioned so as to apply pressure over a cusp and along the elongated axis of a tooth through a predrilled opening in the upper portion of a crown so that opposing pressure may be applied by the upper and lower jaw portions of the instrument to lift and separate a crown from a tooth.

8 Claims, 8 Drawing Figures

DENTAL APPARATUS FOR REMOVING CROWNS

BACKGROUND OF THE INVENTION

1. Field of the Invention

This invention is generally directed to dental instruments or tools for repairing teeth and more specifically to a hand-held plier-like instrument for removing crowns from teeth wherein pressure from the instrument may be selectively aligned by a selectively rotatable pin element carried by the tool so as to assure pressure is applied along the elongated axis of teeth during crown removal.

2. History of the Prior Art

In dentistry, it frequently becomes necessary to repair the exterior portion of a patient's tooth with an artificial cover. Such artificial covers are referred to in the art as crowns or caps. In preparing a tooth for a crown, the crown or cap is prepared for placement by initially molding the crown or cap to serve as the exterior of the tooth and to seat properly on a prepared stub. The damaged exterior portions of the tooth are removed leaving a central stub to which the crown or cap will be cemented or adhesively secured.

It sometimes becomes necessary to remove a crown or cap either because the crown or cap has been damaged or because there is some need to work on the tooth which the crown or cap is covering. Special dental tools or instruments have been designed to remove crowns or caps, however, many of these tools have not proven satisfactorily in actual use or their use has resulted in damage to a tooth and/or the crown.

A number of known crown-removing tools utilize a clamping device which engages the crown in an area adjacent the lower rim or margin thereof and which is urged upwardly with respect to a tooth by use of a bolt or screw which is positioned above the tooth and which engages the upper surface of the tooth through a predrilled opening. As the screw or bolt is threaded towards the tooth, the clamping device is elevated thereby urging the crown from the surface of the tooth. Such prior art removal devices have proven to be structurely complicated and difficult to work with especially in the small work area of a patient's mouth. Additionally, the pressure applied by such devices is generally along a central area of the tooth and their use may result in possible damage to the tooth.

In addition to the foregoing, many prior art devices do not permit a great deal of flexibility in use as the relationship of their component parts is generally fixed. Because of this, such devices or tools will cause pressure to be applied in undesired directions with respect to the elongated axis of a tooth thereby causing patient discomfort and possibly causing damage to the crown and/or the tooth. If the set screw used to urge the crown from a tooth is positioned in a fixed relationship with respect to the other portions of a tool used to remove a crown, the application of pressure may be improperly applied. Some examples of prior art crown removal devices include U.S. Pat. Nos. 4,417,876 to Lynch, 3,755,901 to Wilson et al, 1,858,080 to Flagstad et al., and European Pat. No. 0052497, May 1982.

In addition to the foregoing structures for removing crowns or caps, many dentists have attempted to utilize orthodontic tools to remove crowns. A number of orthodontic instruments resemble pliers having specially prepared ends for working orthodontic bands or braces. Some examples of such orthodontic tools include U.S. Pat. Nos. 1,346,584 to Angle, 2,985,962 to Shiner, 3,755,902 to Northcutt, 3,911,583 to Hoffman, 3,986,265 to Cusato, and 4,248,587 to Kurz. Such orthodontic tools have specially prepared jaw portions and the use of such tools to remove crowns or caps, if at all possible, could result in creating undesirable forces or applications of pressure for removing the crown or the cap from a tooth's surface and thereby possibly cause damage to the crown during removal. In addition, if the pressure is improperly applied during the removal process, damage could occur to the pulp of the tooth which is exposed beneath the crown or cap.

Other types of plier-like tools have been specifically designed for removing crowns or caps. In U.S. Pat. No. 3,834,026 to Klein, a pair of crown-removing pliers is disclosed having opposed arcuately shaped jaw surfaces. The tool is utilized by placing the opposing jaw portions in engagement with opposite sides of the crown. The application of pressure at the handles compresses the jaws towards one another to grasp the crown therebetween. Thereafter the crown is removed by moving the pliers either upwardly and downwardly while applying a slight rocking motion. Such rocking motion applies an undesirable pressure against the tooth and can be discomforting to the patient. In addition, the application of pressure toward or perpendicularly to the axis of the root may make removal more difficult. Clamping the crown against the sides of a tooth creates clamping pressure which must be overcome by any vertical pressure applied to remove a crown.

Other prior art plier-like tools used in dentistry utilize jaws having tapered end portions which form points for engaging both the upper and lower portions of a crown. In use of such tools, it has been necessary to apply a rocking motion in order to pull the lower rim of the crown from the surface of the tooth. Again, such rocking motion causes an undesirable application of pressure perpendicularly with respect to the root of a tooth which can create discomfort for the patient. Also, a rocking motion may result in the destruction of the lower rim or margin of the crown.

SUMMARY OF THE INVENTION

This invention is directed to an apparatus and method for removing dental crowns and caps utilizing a plier-like instrument or tool having opposing jaw portions. One jaw portion is designed to terminate in a slightly hooked and pointed configuration for purposes of engaging the lower rim or margin of a crown or cap. The opposing jaw of the instrument is provided with a rotatable head having a pin member extending therefrom. The pin member is mounted adjacent the outer edge of the rotatable head so as to be selectively and adjustably aligned with respect to the other jaw of the instrument. In use, a hole is first predrilled through the upper portion of the crown preferably over a buccal or lingual cusp and preferably along the central plane of the cusp. The rotating pin member is thereafter brought into alignment with the hole while the opposing pointed jaw portion is brought upwardly against the lower margin of the crown. The application of pressure on the handle of the instrument will cause pressure to be applied through the pin member and along the line of the elongated axis of one of the roots of the tooth while the other jaw applies pressure on the margin of the crown thereby the cement bond between the tooth and crown is broken allowing the crown to be removed.

In a modified embodiment, the fixed jaw portion of the dental instrument may be shaped in a configuration resembling a cross wherein the outer primary tapered point or tip of the tool is supplemented by perpendicularly extending supplemental tip portions. With this embodiment, the primary tip and at least one of the supplementary tips of the fixed jaw of the tool may be selectively aligned for engagement at two space points along the lower margin of the crown to thereby fascilitate the application of pressure along a wider portion of the lower margin of the crown. Additionally, the three points permit interproximal approaches beside the lingual and buccal areas of the tooth.

It is a primary object of this invention to provide a dental instrument which may be utilized to remove crowns from teeth more rapidly than prior art techniques without causing excessive discomfort to a patient and without damaging the crown during the removal process.

It is yet another object of the present invention to provide a crown removing tool which may be utilized in the generally confined space within a patient's mouth and which includes an adjustable pin means for permitting a selective alignment of the working jaws of the tool so that pressure may be properly applied between the opposing jaw portions of the tool to direct any pressure to be transmitted axially of the elongated axis of a root of the tooth and thus preventing the application of any lateral stresses with respect to the elongated axis of the tooth.

It is a further object to the present invention to provide a dental instrument of an uncomplicated structure for removing crowns which may be selectively utilized on various sizes of teeth due to the adjustable relationship between the pressure applying jaws of the instrument with respect to one another.

DESCRIPTION OF THE PREFERRED EMBODIMENT

Figure 1:
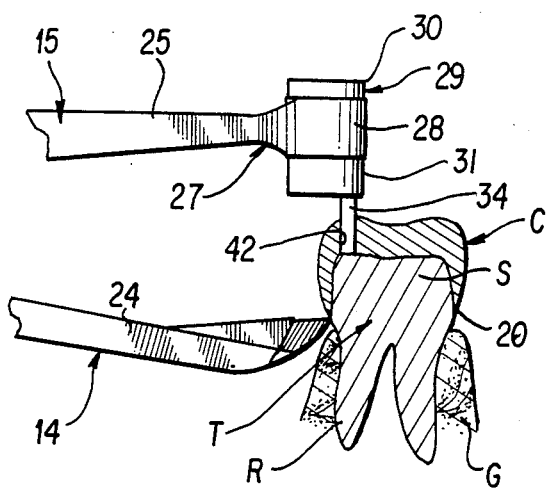
FIG. 1 is a partial perspective view illustrating the work engaging jaws of the dental instrument as they are initially positioned for application of pressure along the elongated axis of a root of a tooth with the lower jaw engaging the lower margin of a crown and the adjustable pin member seated within a predrilled opening in the upper portion of the crown.

With continued reference to the drawings, the dental instrument 10 of the present invention is shown as being a hand held instrument having a general configuration similar to a pair of pliers. The dental tool has a pair of opposed handles 11 and 12 which may be covered with plastic or rubber grips 13. The handles 11 and 12 are integrally formed with outwardly extending jaw portions 14 and 15, respectively, and an intermediate body portions 16 and 17, respectively. The body portions are joined in pivoted relationship by any suitable conventional screw or pin (not shown). As handle 11 and jaw 14 and handle 12 and jaw 15 are both offset on opposite sides of the pivoted connection between body portions 16 and 17, movement of the handles toward one another will cause the jaws to also close with respect to one another.

The dental instrument 10 is uniquely and specifically designed for use in removing dental crowns C which have previously been affixed to a prepared and shaped stub S of a tooth T having roots R. The removal of crowns may be necessary to permit further repair to the underlying tooth, to replace a damaged crown, to remove a bridge when one end is loose, or to remove the crown for endodontic purposes.

Figure 2:
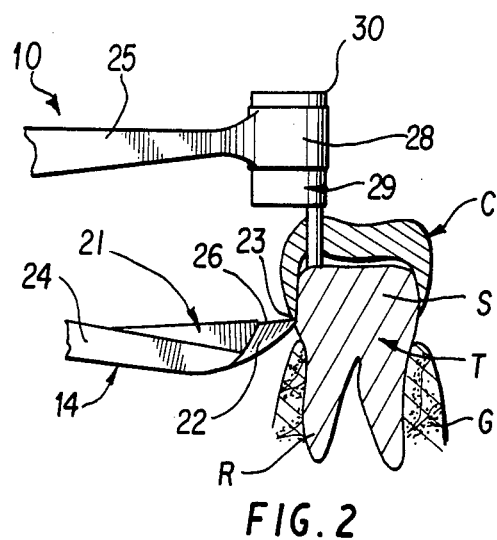
FIG. 2 is a partial perspective view illustrating the dental instrument of the present invention and showing the upward displacement of a crown with respect to the underportion of a tooth after pressure has been applied to the handles of the tool.
Figure 3:
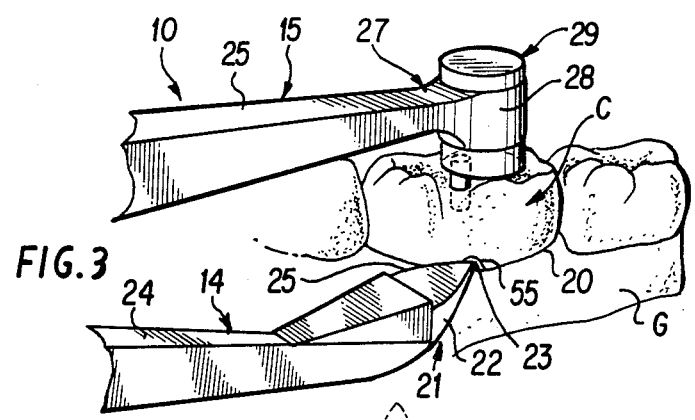
FIG. 3 is a perspective view illustrating the dental instrument of the present invention as it is positioned to remove a crown from a tooth.

The lower or fixed jaw 14 of the dental instrument is designed to cooperatively engage the lower edge or margin 20 of the crown C. With particular reference to FIGS. 1-3, the end portion 21 of the lower jaw 14 includes a tapered portion 22 which terminates to form a point 23 which is oriented outwardly and toward the opposed jaw 15. The tapered portions of the jaw create an arcuate outer edge which extends convexly from the point 23 toward the center portion 24 of the jaw 14. The configuration of the tip permits the jaw to be oriented adjacent to the lower margin of the crown C without interfering with a patient's gum G. In this regard, the upper side edges 25 of the end portion of jaw 14 are also sharply defined so that such edges may alternately be utilized to engage the lower margin of the crown.

Figure 5:
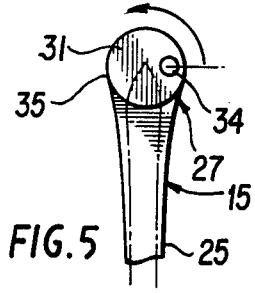
FIG. 5 is a partial bottom plan view showing the upper rotatable jaw portion of the dental instrument with the lower jaw portion shown in dotted line.

The upper jaw 15 of the dental instrument 10 includes an elongated central portion 26 and an end portion 27. The end of the upper jaw is formed into a circular ring or sleeve 28. A stub shaft member 29 is mounted within the sleeve 28 in such a manner that the shaft is rotatable about its central axis (about an axis generally perpendicular to the length of the jaw 15 as shown by the arrow in FIG. 5). The stub shaft is shown as having end portions 30 and 31 which are of an enlarged diameter so as to prevent the displacement of the shaft 29 from within the sleeve 28.

A generally cylindrical pin member 34 extends outwardly from end portion 30 of the stub shaft 29 and is positioned adjacent the outer edge 35 thereof so as to be offset from the axis of the shaft 29. In this manner, the pin member may be selectively maneuvered into an adjusted position in a circular path or orbit about the axis of the shaft. Therefore, the opposing relationship and/or alignment between the pin member 34 and the end portion of the lower jar 14 may be selectively altered or changed. As further shown in FIG. 5, the adjustable alignment between the pin and the end portion of the lower jaw permits the pin to either be positioned outwardly beyond the point of the end portion or inwardly thereof. This selective alignment between the pin member and the lower jaw of the dental instrument permits the instrument to be adjusted to apply pressure to a number of positions with respect to the upper surface of the crown which is extremely important and beneficial for reasons that will be discussed in greater detail hereinafter.

The dental instrument of the present invention is preferably constructed using a surgical grade stainless steel material with the tip or end poritons of the jaws being reinforced with a carbide or other hardened steel alloy. Although the size of the tool may vary, it is preferred that the pin member generally by 4 to 5 mm in length and approximately 1 to 2 mm in diameter.

In use of the dental instrument 10, the patient's crown should first be thoroughly surveyed or inspected. It is preferred, if possible, to align the pin member of the instrument over the tip area of a tooth cusp and in general vertical alignment with a portion of the lower margin of the crown which may be engaged by the tip or end portion of the lower jaw of the tool. The general principle is to insure that pressure is applied from the pin member along the elongated axis of the tooth and therefore along the line of a root.

Figure 4:
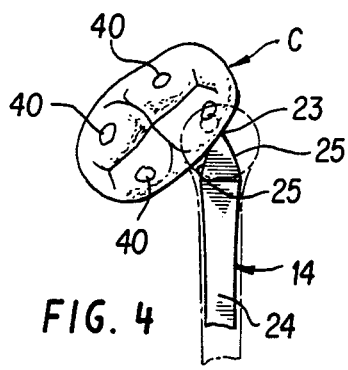
FIG. 4 is a partial top plan view having portions broken away showing the lower jaw of the dental instrument engaging the lower margin of a crown with the upper jaw shown in dotted line.

With specific reference to FIG. 4, there are four small circles shown at 40 which identify the preferred areas or locations for applying pressure through the pin member to a tooth. It is important to avoid placing pressure toward the central pulpal area of the tooth, as the pulp could be injured or damaged if pressure is applied in this region. The preferred or recommended areas are generally in the region over the mesial or distal buccal or lingual cusps and perhaps slightly toward the central planes of the cusps. The four points 40 shown are generally over the occlusal surface and inside the buccal and lingual cusp margins of the tooth.

In order to prepare the upper surface of the crown to receive the pin member, a hole 42 is drilled in the vicinity of one of the recommended areas 40 of the crown at a point where the tip or end portion of the lower jaw of the instrument can engage the lower margin of the crown. The hole 42 should be drilled 1 to 2 mm in depth and generally not greater than 2 mm. The hole should be drilled until dentin, cement or filing is initially contacted. The diameter of the hole should be slightly larger than the diameter of the pin member, i.e., about the size of a 1559 bur. In the event sound tooth material is not located after drilling 2 mm, it is advisable to select an alternative location for the hole where penetration of the crown is within the 1 to 2 mm depth over a cusp.

Once the hole 42 is prepared, the pin member 34 is rotated to the proper position to permit its vertical alignment within the hole. An edge 25 or point 23 of the tip or end portion of the lower jaw 14 of the instrument is subsequently urged into engagement with the lower marginal edge 20 of the crown C. The pin member should be maintained as vertically aligned with the elongated axis of the tooth as possible so that the pressure applied to the tooth is transmitted along the elongated axis thereof. The lower jaw 14 of the instrument should also be aligned to provide a vertical pressure adjacent the side of the tooth. With the dental instrument in proper position, controlled pressure is increasingly applied to the handles to lift the crown from the prepared tooth. Care should be taken to retaining the patient's cheek and tongue spaced from the jaws of the instrument so that they will not be pinched by the closing action of the jaws of the plier-like instrument.

Figure 6:
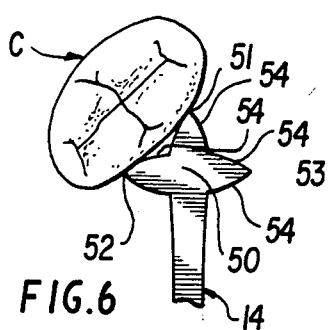
FIG. 6 is a modified form of the invention showing the lower fixed jaw portion of the dental instrument in a general cross-like configuration wherein the lower margin of the crown may be engaged at two spaced points.
Figure 7:
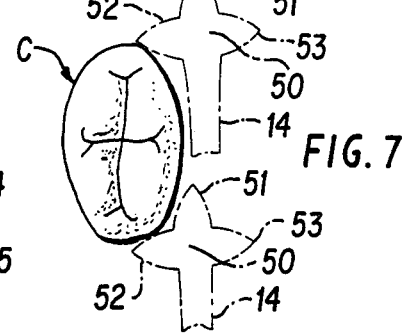
FIG. 7 is a partial top plan view of the modified form of the invention of FIG. 6 showing two separate interproximal approaches to the crown.
Figure 8:
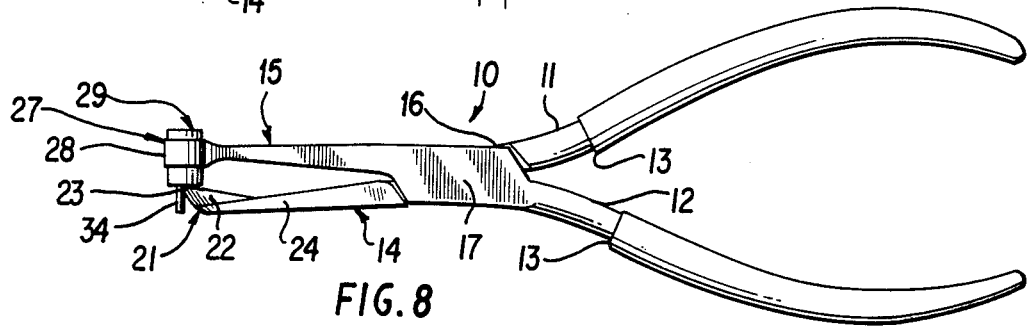
FIG. 8 is a perspective view of the dental instrument of the present invention.

With particular reference to FIGS. 6 and 7 of the drawings, an alternate embodiment of the invention is disclosed. In this embodiment, the lower jaw 14 of the instrument is shown as having a cross shaped tip or end portion 50 with a central point 51 and outwardly extending side points 52 or 53. The shape of the central point 51 is generally the same as the shape described with respect to the point 23 of the preferred embodiment. The side points 52 and 53 are generally spaced approximately 3 mm from the end of the central point 51 and extend outwardly a distance equal to approximately 1 mm. The side edges 54 of the supplemental points are also sharply defined so as to be useful in engaging the lower margin of the crown at many points and with different instrument approaches. The cross shaped tip 50 can be used to permit pressure to be applied at two spaced points or locations along the lower margin of the crown as shown at FIG. 6 or at interproximal mesial and distal approaches as shown at the two dotted line positions of FIG. 7.

In the event the lower margin of the crown is below the gum line or is too smooth to permit a secure engagement by the end portions of the lower jaws of either the preferred or alternate embodiments of the invention, a small notch 55 (FIG. 3) should be formed in the lower area of the crown approximately 1 to 2 mm above the gingivae. The notch 55 may be cut using a number 37 or 38 inverted cone bur or similar tool. However, the shallow notch or purchase point should not be drilled completely through the crown material. It is sufficient to provide a shallow notch in which the edges or points of the tips or ends of the lower jaw may be engaged.

I claim:

1. A dental apparatus for removing crowns from teeth comprising a pair of handle members which are integrally formed with outwardly extending first and second intermediate portions and first and second jaw portions, respectively, said intermediate portions being pivotally joined so that said first and second jaw portions are movable toward one another when said handle means are moved toward one another, said first jaw portion having a tapered tip which converges to an end point, said second jaw portion having a tip portion, a rotatable shaft carried by said tip so as to be rotatable about the elongated axis of said shaft which extends generally perpendicular to said second jaw portion, a pin means carried by said shaft and extending outwardly therefrom toward said first jaw portion and extending in spaced but generally parallel relationship to said elongated axis of said shaft whereby said pin means and said end point of said first jaw portion of said apparatus may be selectively aligned by the rotational reorientation of said pin means.

2. The dental apparatus of claim 1 in which said tip of said first jaw portion is tapered upwardly and outwardly to said end point, a pair of sharply defined edges extending from said end point inwardly of said first jaw portion.

3. The dental apparatus of claim 2 in which said tip portion includes a hollow sleeve means, said rotatable shaft being disposed within said sleeve means.

4. The dental apparatus of claim 3 in which said rotatable shaft has upper and lower enlarged ends which prevent said shaft from being displaced with respect to said sleeve means.

5. The dental apparatus of claim 4 in which said pin means extends outwardly from said lower enlarged end of said rotatable shaft, said lower end having an outer periphery, said pin means being located adjacent said outer periphery of said lower end.

6. The dental apparatus of claim 1 in which said tapered tip of said first jaw portion includes at least one supplemental point spaced inwardly of said end point, said supplemental point extending outwardly at an angled relationship with respect to said end point so that said supplemental point and said end point may be selectively used alone or in combination to thereby permit the apparatus to be used with varying approaches to the margin of the crown.

7. The dental apparatus of claim 6 including two supplemental points which extend outwardly on opposite sides of said tapered tip of said first jaw portion so as to be on opposite sides of said end point, said supplemental points and said end point forming a generally cross-shaped configuration.

8. A method of removing dental crowns having upper portions and lower marginal edges from teeth using a plier-like tool having one jaw supporting a pin member and the opposing jaw having a pointed end portion comprising the steps of:

A. drilling a hole through the upper portion of the crown at a point above the elongated axis of the root of a tooth and in the area above a buccal or lingual cusp;

B. forming a notch in the crown adjacent the lower marginal edge thereof;

C. aligning the pin member of the plier-like tool within the hole drilled in the upper portion of the crown;

D. positioning the pointed end portion of the opposing jaw of the tool within said notch;

E. applying pressure to the plier-like tool to urge the jaws thereof toward one another thereby lifting the crown from the tooth.

* * * * *